(12) United States Patent
Subramaniam et al.

(10) Patent No.: US 10,751,319 B2
(45) Date of Patent: Aug. 25, 2020

(54) COLLECTION DEVICE AND METHODS FOR USE

(71) Applicant: CRITITECH, INC., Lawrence, KS (US)

(72) Inventors: Bala Subramaniam, Lawrence, KS (US); Jahna Espinosa, Lawrence, KS (US); Greg Johnson, Wichita, KS (US); Jacob M. Sittenauer, Lawrence, KS (US); Joseph S. Farthing, Lawrence, KS (US)

(73) Assignee: Crititech, Inc., Lawrence, KS (US)

(*) Notice: Subject to any disclaimer, the term of this patent is extended or adjusted under 35 U.S.C. 154(b) by 186 days.

(21) Appl. No.: 15/573,091

(22) PCT Filed: Jun. 6, 2016

(86) PCT No.: PCT/US2016/036013
§ 371 (c)(1),
(2) Date: Nov. 9, 2017

(87) PCT Pub. No.: WO2016/197101
PCT Pub. Date: Dec. 8, 2016

(65) Prior Publication Data
US 2018/0116910 A1     May 3, 2018

Related U.S. Application Data

(60) Provisional application No. 62/171,001, filed on Jun. 4, 2015, provisional application No. 62/171,060, filed
(Continued)

(51) Int. Cl.
*A61K 31/337* (2006.01)
*A61K 9/00* (2006.01)
(Continued)

(52) U.S. Cl.
CPC ............... *A61K 31/337* (2013.01); *A61J 3/02* (2013.01); *A61K 9/0019* (2013.01); *A61K 9/10* (2013.01);
(Continued)

(58) Field of Classification Search
CPC .. A61K 31/337; A61K 9/1682; A61K 9/5192; A61K 9/1605; A61K 9/1688;
(Continued)

(56) References Cited

U.S. PATENT DOCUMENTS 3,648,698 A * 3/1972 Doherty .............. A61M 1/0017
604/319
5,143,528 A     9/1992 Dongelmans
(Continued)

FOREIGN PATENT DOCUMENTS

DE     3120047 A1 * 12/1982 .......... A61M 1/0001
EP     2 258 748 A1    12/2010
(Continued)

OTHER PUBLICATIONS

English language machine translation of DE 3120047 A1, Generated Dec. 6, 2019. (Year: 2019).*
(Continued)

*Primary Examiner* — David C Mellon
(74) *Attorney, Agent, or Firm* — McDonnell Boehnen Hulbert & Berghoff LLP (57) ABSTRACT

The present disclosure provides an apparatus and methods of use for collecting particles. An example collection device includes (a) a vessel defining a chamber, wherein the vessel includes a distal end and a proximal end, (b) an inlet port extending from the proximal end of the vessel, wherein the inlet port is in fluid communication with the chamber, and (c) an outlet port extending from the proximal end of the vessel, wherein the inlet port is in fluid communication with
(Continued)

the chamber, and wherein the outlet port includes a porous material positioned between the chamber and the outlet port.

14 Claims, 4 Drawing Sheets

Related U.S. Application Data on Jun. 4, 2015, provisional application No. 62/171,008, filed on Jun. 4, 2015.

(51) Int. Cl.
| | |
|---|---|
| A61K 9/10 | (2006.01) |
| A61K 9/14 | (2006.01) |
| A61K 9/16 | (2006.01) |
| B01J 19/10 | (2006.01) |
| B01J 19/26 | (2006.01) |
| B01J 2/04 | (2006.01) |
| B01J 3/00 | (2006.01) |
| B01J 4/00 | (2006.01) |
| A61K 9/51 | (2006.01) |
| A61J 3/02 | (2006.01) |
| B01D 46/24 | (2006.01) |
| B01J 3/02 | (2006.01) |
| B05B 1/34 | (2006.01) |
| B05B 13/02 | (2006.01) |

(52) U.S. Cl.
CPC ............. *A61K 9/14* (2013.01); *A61K 9/1605* (2013.01); *A61K 9/1682* (2013.01); *A61K 9/1688* (2013.01); *A61K 9/5192* (2013.01); *B01D 46/24* (2013.01); *B01J 2/04* (2013.01); *B01J 3/008* (2013.01); *B01J 3/02* (2013.01); *B01J 4/002* (2013.01); *B01J 19/10* (2013.01); *B01J 19/26* (2013.01); *B05B 1/3489* (2013.01); *B05B 13/0278* (2013.01); *B01D 2271/02* (2013.01); *B05D 2401/90* (2013.01)

(58) Field of Classification Search
CPC .......... A61K 9/14; A61K 9/10; A61K 9/0019; B01J 3/02; B01J 4/002; B01J 3/008; B01J 2/04; B01J 19/26; B01J 19/10; B01D 46/24; B01D 2271/02; B01D 11/0203; B01D 11/0411; B01D 11/0407; B01D 11/0403; B01D 46/00; B01D 46/543; B01D 46/54; B01D 46/10; B01D 46/106; B01D 46/103; A61J 3/02; B05D 2401/90; B05B 1/341; B05B 13/0278; B05B 1/3489; B01L 3/50; B01L 3/502; B01L 3/5021; B01L 3/5023; B01L 3/505; B01L 3/508; B01L 3/5082; B01L 3/50825; B01L 2200/0631; B01L 2300/04; B01L 2300/041; B01L 2300/042; A61M 1/0001; A61M 1/0005; A61M 1/0011; A61M 1/0017

See application file for complete search history.

(56) References Cited

U.S. PATENT DOCUMENTS

| | | | | |
|---|---|---|---|---|
| 5,409,833 | A * | 4/1995 | Hu | A61F 2/062 422/421 |
| 6,916,389 | B2 * | 7/2005 | Pesiri | B01F 3/0861 149/109.6 |
| 8,778,181 | B1 | 7/2014 | Johnson et al. | |
| 8,888,753 | B2 * | 11/2014 | Romano | A61M 1/0001 604/319 |
| 2003/0144646 | A1 * | 7/2003 | Se | A61M 1/02 604/409 |
| 2008/0010956 | A1 * | 1/2008 | Fogelman | B01D 11/0203 55/319 |
| 2011/0209578 | A1 * | 9/2011 | Ara | B01J 19/10 75/345 |
| 2012/0103536 | A1 * | 5/2012 | Hubbard, Jr. | B01D 1/18 159/4.01 |
| 2018/0169945 | A1 * | 6/2018 | Chanclon Fernandez | B28B 1/001 |
| 2019/0224245 | A1 * | 7/2019 | Katz | B01D 21/262 |

FOREIGN PATENT DOCUMENTS

| | | |
|---|---|---|
| JP | S59-058019 U | 4/1984 |
| JP | H07-047194 A | 2/1995 |
| JP | H11-189403 A | 7/1999 |
| JP | 2003-251127 A | 9/2003 |
| WO | 1995/01221 A1 | 1/1995 |
| WO | 2005/054130 A1 | 6/2005 |

OTHER PUBLICATIONS

The International Search Report (ISR) for PCT/US2016/036013 dated Aug. 30, 2016, pp. 1-4.
Written Opinion of the International Searching Authority for PCT/US2016/036013 dated Aug. 30, 2016, pp. 1-5.

* cited by examiner

COLLECTION DEVICE AND METHODS FOR USE

CROSS REFERENCE

This application is a U.S. national phase of International Application No. PCT/US2016/036013, filed on Jun. 6, 2016, which claims priority to U.S. Provisional Application No. 62/171,001, filed Jun. 4, 2015; U.S. Provisional Application No. 62/171,060, filed Jun. 4, 2015; and U.S. Provisional Application No. 62/171,008, filed Jun. 4, 2015, all of which are incorporated by reference herein in their entirety.

BACKGROUND

A need exists for apparatuses and methods capable of producing sub-micron and nano-sized particles. The need is particularly pronounced in the field of pharmaceutics. Conventional techniques for particle-size reduction currently practiced suffer from many disadvantages. As such, a need remains for improved equipment and processes for the preparation, harvesting and collection of small particles.

SUMMARY OF THE INVENTION

In one aspect, the invention comprises a collection device, including (a) a vessel defining a chamber, wherein the vessel includes a distal end and a proximal end, (b) an inlet port extending from the proximal end of the vessel, wherein the inlet port is in fluid communication with the chamber, and (c) an outlet port extending from the proximal end of the vessel, wherein the outlet port is in fluid communication with the chamber, and wherein the outlet port includes a porous material positioned between the chamber and the outlet port.

In a second aspect, the invention includes a method for isolating particles comprising (a) providing a collection device including (i) a vessel defining a chamber, (ii) an inlet port in fluid communication with the chamber, (iii) an outlet port in fluid communication with the chamber, wherein the outlet port includes a porous material positioned between the chamber and the outlet port, and (iv) a sampling tube having a distal end and a proximal end, wherein the proximal end of the sampling tube extends from the proximal end of the vessel, and wherein the distal end of the sampling tube extends into the chamber, (b) receiving a plurality of particles through the inlet port of the particle collection device, (c) collecting the plurality of particles in the chamber of the vessel, (d) receiving a gas through the inlet port, and (e) venting the gas through the porous material and out of the outlet port.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

All references cited are herein incorporated by reference in their entirety. As used herein, the singular forms "a", "an" and "the" include plural referents unless the context clearly dictates otherwise. "And" as used herein is interchangeably used with "of" unless expressly stated otherwise. All embodiments of any aspect of the invention can be used in combination, unless the context clearly dictates otherwise.

As used herein, "about" means+/−5% of the recited value.

In one aspect, the present invention comprises a collection device, including (a) a vessel defining a chamber, wherein the vessel includes a distal end and a proximal end, (b) an inlet port extending from the proximal end of the vessel, wherein the inlet port is in fluid communication with the chamber, and (c) an outlet port extending from the proximal end of the vessel, wherein the outlet port is in fluid communication with the chamber, and wherein the outlet port includes a porous material positioned between the chamber and the outlet port.

Figure 1:
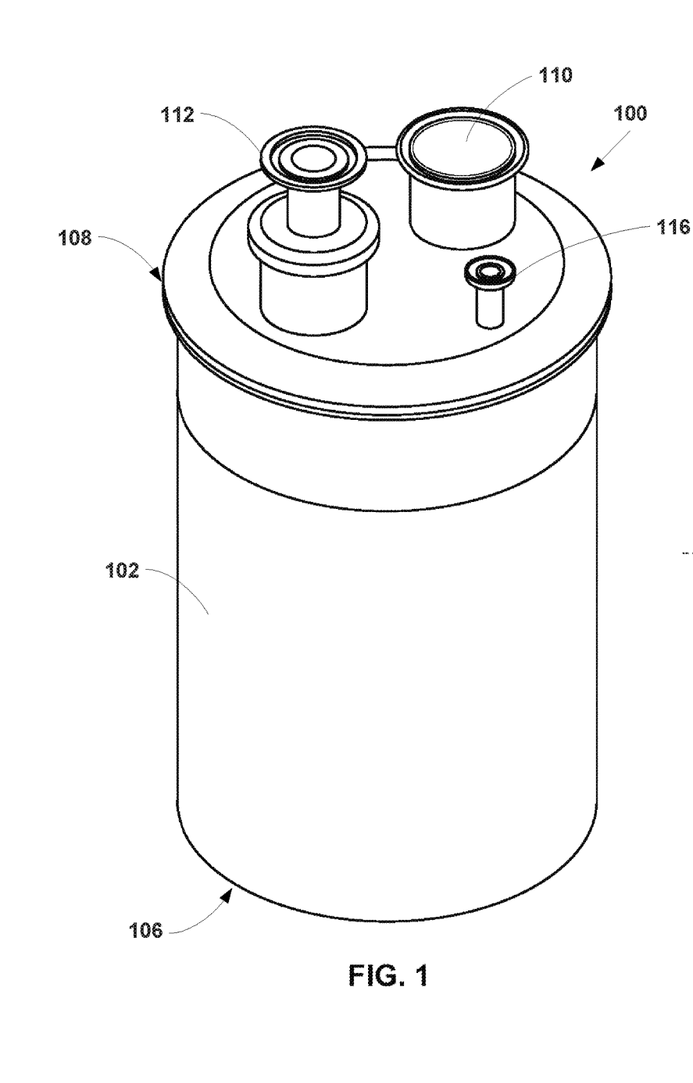
FIG. 1 illustrates a perspective view of a particle collection device, according to an example embodiment.
Figure 3:
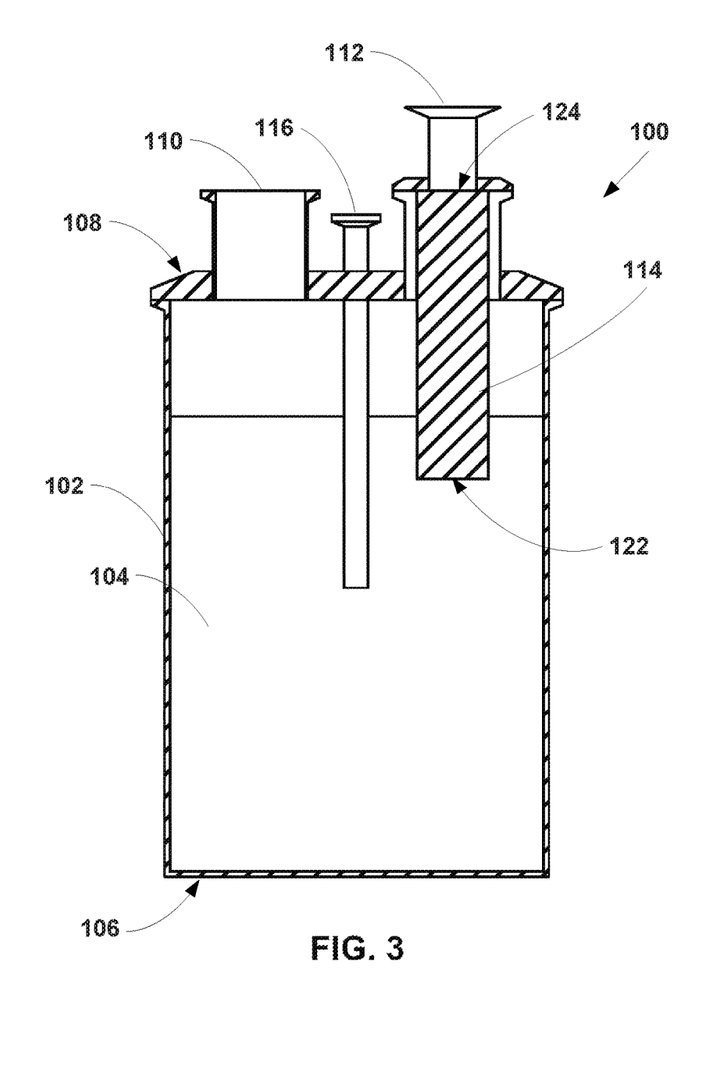
FIG. 3 illustrates a cross-section view of the particle collection device, according to an example embodiment.
Figure 4:
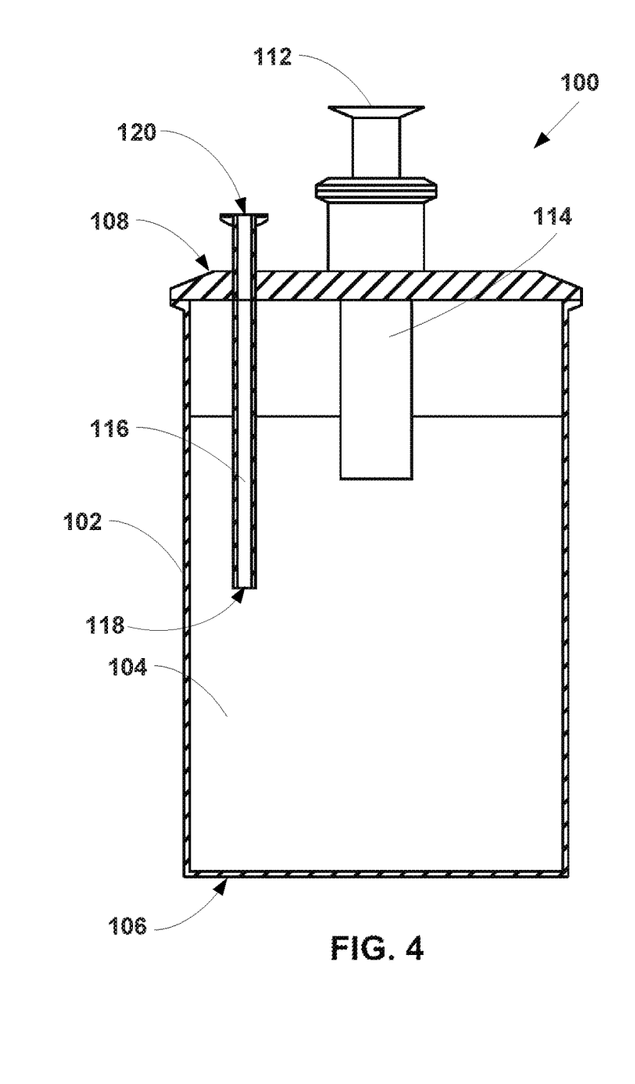
FIG. 4 illustrates another cross-section view of the particle collection device, according to an example embodiment.

With reference to the Figures, as shown in FIG. 1, the invention comprises a collection device 100 including a vessel 102 defining a chamber 104. The vessel 102 includes a distal end 106 and a proximal end 108. The outer diameter of the vessel 102 may range from about 152.4 mm to about 914.4 mm. The collection device 100 further includes an inlet port 110 extending from the proximal end 108 of the vessel 102. The inlet port 110 is in fluid communication with the chamber 104. The inlet port 110 may have an outer diameter ranging from about 12.7 mm to about 101.6 mm. Further, the collection device 100 includes an outlet port 112 extending from the proximal end 108 of the vessel 102. As shown in FIGS. 3 and 4, the outlet port 112 is in fluid communication with the chamber 104, and the outlet port 112 includes a porous material 114 positioned between the chamber 104 and the outlet port 112. The outer diameter of the outlet port may range from about 12.7 mm to about 50.8 mm.

As shown in FIGS. 1-4, the collection device 100 may further include a sampling tube 116 having a distal end 118 and a proximal end 120. The outer diameter of the sampling tube 116 may range from about 6.35 mm to about 25.4 mm. As shown in FIGS. 3 and 4, the proximal end 120 of the sampling tube 116 extends from the proximal end 108 of the vessel 102, and the distal end 118 of the sampling tube 116 extends into the chamber 104. The sampling tube 116 may be configured to remove a small sample of particles from the chamber 104 during a particle production run in which additional particles are being formed. In particular, the sampling tube 116 may include a sample thief that enables an operator to remove a small sample of particles without opening the chamber 104 or removing the sampling tube 116 from the rest of the collection device 100 during processing. This enables an operator to test a small sample of particles to ensure that the product is within specifications as the process continues to run. For example, particle size or residual solvent analysis may be performed on the sample. If the measured specifications do not match the desired specifications, the operating parameters of the particle formation process may be suitably adjusted to correct the situation before an entire batch of product with undesirable characteristics is created.

The porous material 114 positioned between the chamber 104 and the outlet port 112 may take a variety of forms. In one example, the porous material 114 is selected from the group consisting of a frit, a mesh, a cloth. As one specific example, the porous material 114 may comprise a high-efficiency particulate arrestance (HEPA) filter. An example HEPA filter may include a mat of randomly arranged fibers, the fibers composed of fiberglass and possessing diameters between about 0.5 micrometers and about 2.0 micrometers. In another example, the porous material 114 comprises a sintered filter having a distal end 122 and a proximal end 124. In such an example, the proximal end 124 of the sintered filter extends from the proximal end 108 of the vessel 102 and is coupled to the outlet port 112, and the distal end 122 of the sintered filter extends into the chamber 104. Such a sintered filter may include a porous stainless steel filter cartridge, as an example. Other porous materials are possible as well.

The inlet port 110 may include a coupling mechanism connecting an outlet of a particle filtration system to the inlet port 110. In one example, the coupling mechanism comprises one or more sanitary fittings. In another example, the coupling mechanism comprises a threaded connection between the outlet of the particle filtration system to the inlet port 110. In yet another example, the coupling mechanism comprises one or more compression fittings. Other example coupling mechanisms are possible as well.

Figure 5:
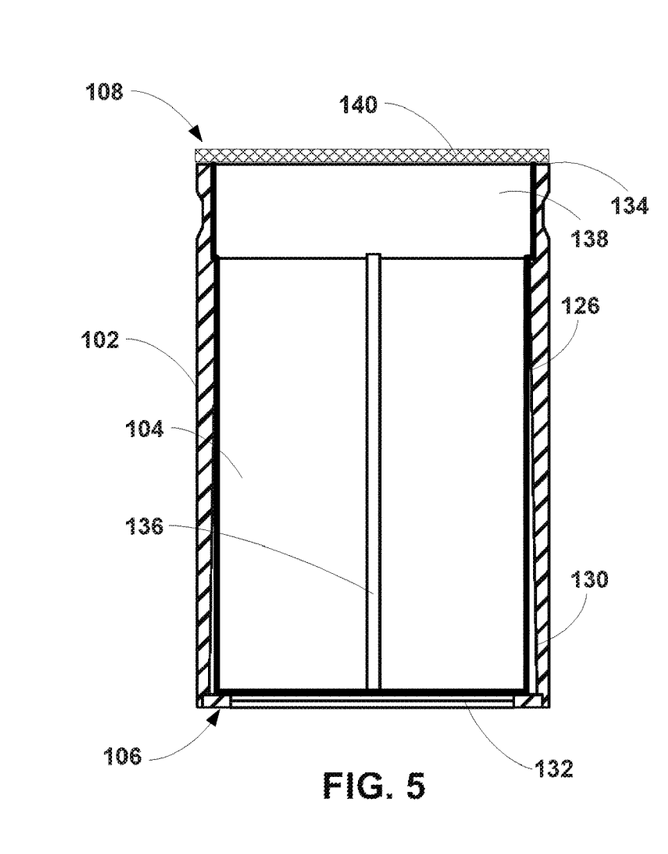
FIG. 5 illustrates another cross-section view of the particle collection device, according to an example embodiment.
Figure 6:
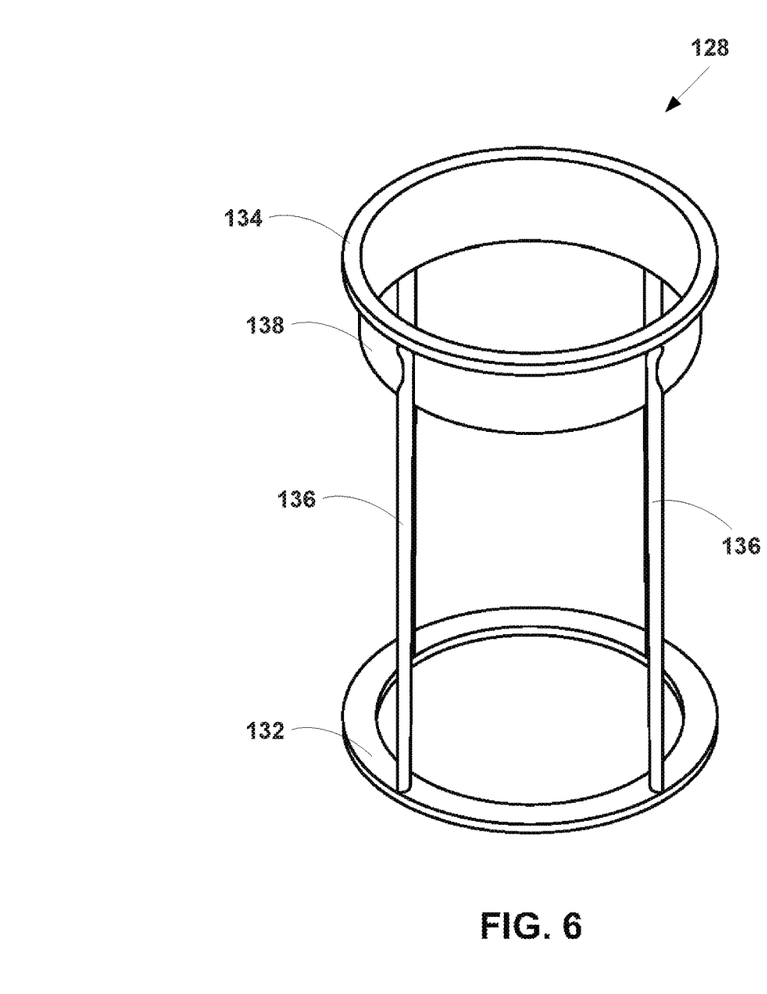
FIG. 6 illustrates a perspective view of a support frame, according to an example embodiment.

Further, as shown in FIG. 5, the collection device 100 may further include a collection insert 126 positioned within the chamber 104 of the vessel 102, and a support frame 128 positioned between an interior wall 130 of the chamber 104 and the collection insert 126. The collection insert 126 may be a plastic bag, as an example. As shown in FIG. 6, the support frame 128 may include a distal ring 132, a proximal ring 134, one or more support legs 136 connecting the distal ring 132 to the proximal ring 134, and a gasket 138 positioned adjacent to the proximal ring 134. In one example, the gasket 138 may comprise a neoprene gasket. The vessel 102 may include a removable lid 140 that can be removed to access the collection insert 126 once particle collection is completed. In such an example, the collection insert 126 may be positioned within the chamber 104 of the vessel 102 such that top edge of the collection insert 126 folds over the top of the support frame 128 and is sealed between the gasket 138 and the removable lid 140 when the lid is in the closed position. Other arrangements are possible as well.

Further still, the components of the collection device 100 may be a part of a larger particle production system. Such a particle production system may include one or more nozzle assemblies, a sonic energy source positioned adjacent to the orifice of each nozzle, one or more particle filtration systems in communication with one or more nozzle assemblies, and one or more particle collection devices, such as those described above, each in communication with the one or more particle filtration systems. In one example, the one or more particle filtration systems comprise a tandem particle filtration system including at least one high pressure harvesting filter system and at least one low pressure collection filter system in tandem and downstream to the harvesting filter. In such an example, the particle production system may include at least two particle harvesting filters, two particle collection filters and two collection devices.

In one example, the nozzle assembly includes (a) a vessel defining a pressurizable chamber, wherein the vessel includes a distal end and a proximal end. (b) an inlet of the pressurizable chamber at the proximal end of the vessel, (c) a nozzle positioned within the pressurizable chamber, wherein the nozzle includes an inlet tube in fluid communication with the inlet of the pressurizable chamber, wherein the nozzle includes an outlet aperture, wherein the nozzle is adjustable to alter a distance between the proximal end of the vessel and the outlet aperture of the nozzle, and wherein the nozzle is adjustable to alter an angle between a longitudinal axis of the vessel and a longitudinal axis of the nozzle, and (d) an outlet of the pressurizable chamber at the distal end of the vessel. In such an example, the inlet port 110 of the collection device 100 may be coupled to the outlet of the pressurizable chamber of the nozzle assembly.

In various embodiments, the one or more particle formation systems comprise one or more high pressure supercritical fluid (SCF) particle formation systems. In such an example, the one or more high pressure SCF particle formation systems may include a pressurizable precipitation chamber including a SCF inlet, a process fluid inlet, and a fluid outlet, and a process fluid disperser to disperse process fluid into the precipitation chamber. Any suitable pressurizable chamber may be used, including but not limited to those disclosed in U.S. Pat. Nos. 5,833,891 and 5,874,029.

In another example, the particle production system comprises at least one of a) two particle harvesting filters, two particle collection filters and two collection devices: b) two particle harvesting filters, one particle collection filter and one or more collection devices; c) two particle harvesting filters, two particle collection filters and one or more collection devices; d) two particle harvesting filters, one particle collection filter and one or more collection devices: e) two tandem filter particle harvesting and collection devices arranged in parallel; f) two or more particle harvesting filters arranged in parallel, one particle collection filter and two or more collection devices arranged in parallel; g) two or more precipitation chambers; h) at least two tandem filter particle filtration systems; i) at least two collection devices; or j) a combination thereof.

In another aspect, the invention provides methods for isolating particles comprising (a) providing a collection device including (i) a vessel defining a chamber, (ii) an inlet port in fluid communication with the chamber, (iii) an outlet port in fluid communication with the chamber, wherein the outlet port includes a porous material positioned between the chamber and the outlet port, and (iv) a sampling tube having a distal end and a proximal end, wherein the proximal end of the sampling tube extends from the proximal end of the vessel, and wherein the distal end of the sampling tube extends into the chamber, (b) receiving a plurality of particles through the inlet port of the particle collection device, (c) collecting the plurality of particles in the chamber of the vessel, (d) receiving a gas through the inlet port, and (e) venting the gas through the porous material and out of the outlet port.

FIG. 7 is a block diagram of a method 200, according to an example embodiment. Method 200 shown in FIG. 7 presents an embodiment of a method that could be used with the collection device 100 of FIGS. 1-6, for example. Method 200 may include one or more operations, functions, or actions as illustrated by one or more of blocks 202-210. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

Figure 7:
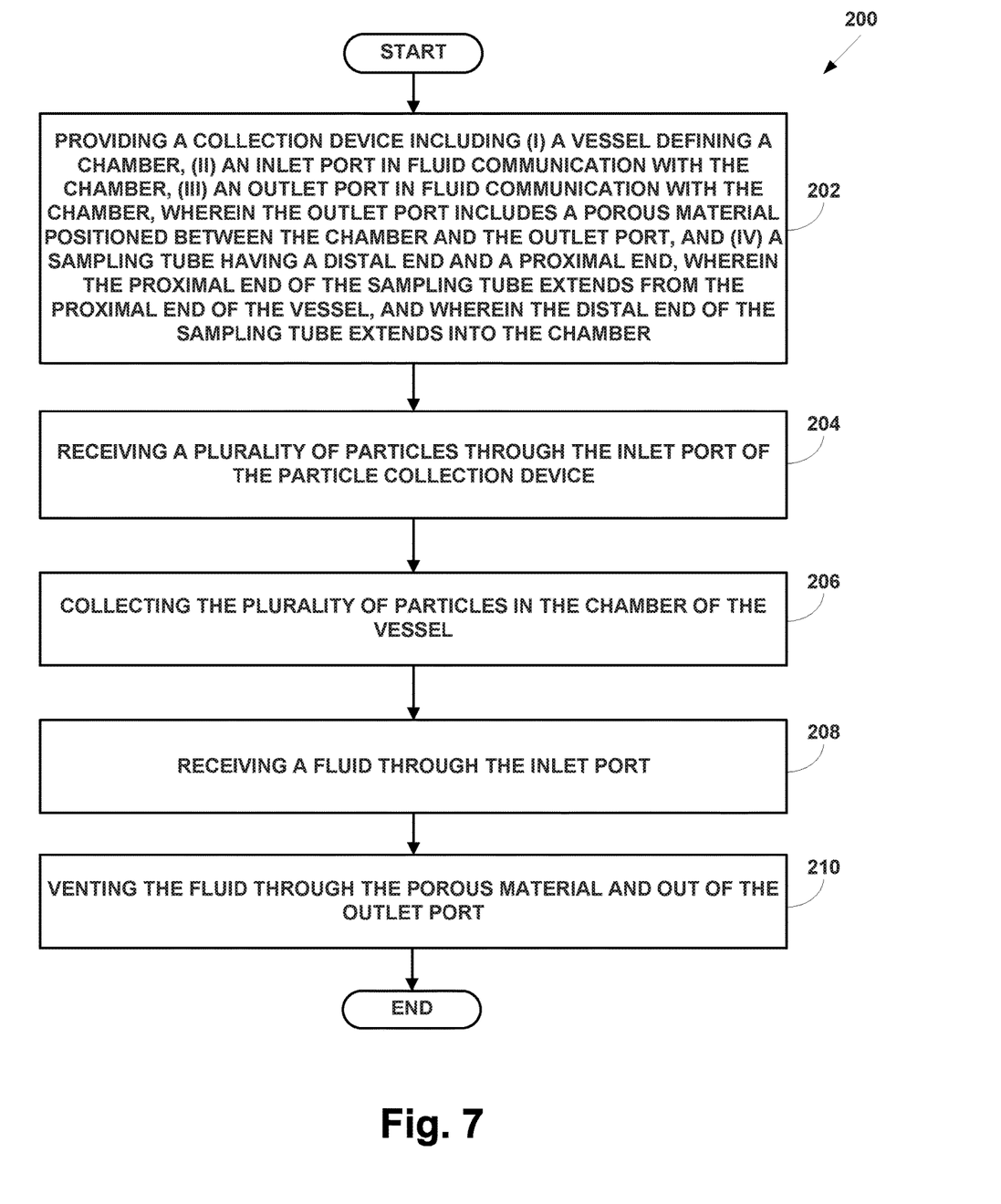
FIG. 7 is a block diagram of a method, according to an example embodiment.

In addition, for the method 200 and other processes and methods disclosed herein, the flowchart shows functionality and operation of one possible implementation of present embodiments. In this regard, each block may represent a module, a segment, a portion of a manufacturing or operation process, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Figure 2:
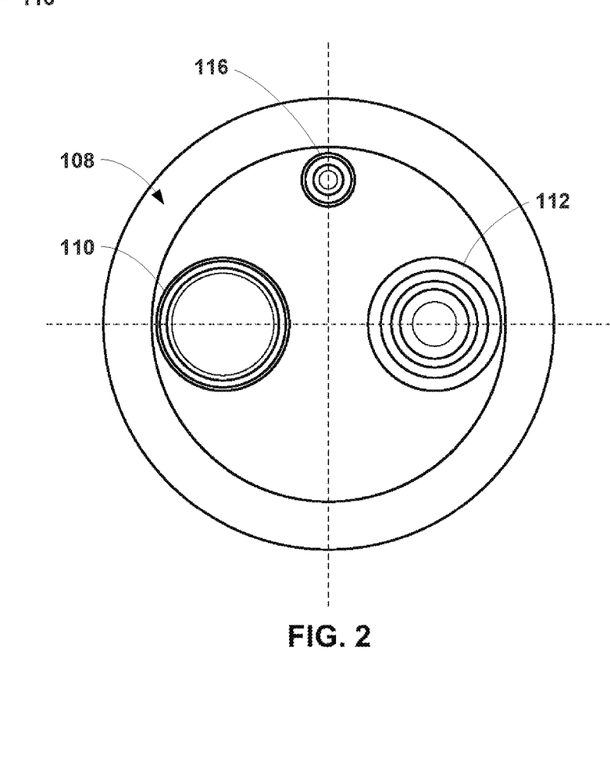
FIG. 2 illustrates a top view of the particle collection device, according to an example embodiment.

In addition, for the method 200 and other processes and methods disclosed herein, each block in FIG. 2 may represent circuitry that is wired to perform the specific logical functions in the process.

At block 202, the method 200 includes providing a collection device including (i) a vessel defining a chamber, (ii) an inlet port in fluid communication with the chamber, (iii) an outlet port in fluid communication with the chamber, wherein the outlet port includes a porous material positioned between the chamber and the outlet port, and (iv) a sampling tube having a distal end and a proximal end, wherein the proximal end of the sampling tube extends from the proximal end of the vessel, and wherein the distal end of the sampling tube extends into the chamber.

At block 204, the method 200 includes receiving a plurality of particles through the inlet port of the particle collection device. At block 206, the method 200 includes collecting the plurality of particles in the chamber of the vessel. At block 208, the method 200 includes receiving a gas through the inlet port. At block 210, the method 200 includes venting the gas through the porous material and out of the outlet port. Venting the gas through the porous material and out of the outlet port enables the separation of the produced particles from the gases, such as gaseous CO2.

In one embodiment, the method 200 further includes the steps of removing the plurality of particles from the chamber of the vessel. In yet another embodiment, the method further includes the steps of sampling one or more particles from the sampling tube, and adjusting one or more parameters of the particle formation system in response to the sampled one or more particles.

EXAMPLES

Materials and Methods

Raw paclitaxel and docetaxel were purchased from Phyton Biotech (British Columbia, Canada), lot number FP2-15004 and DT7-14025, respectively. Both were characterized in their raw form. The milling of both drugs was accomplished using a Deco-PBM-V-0.41 mill (Deco). The milling conditions for both compounds were as follows:

Ball size=5 mm
RPM=600
Processing time=60 min
Room temperature.

Preparation of Paclitaxel Particles

A solution of 65 mg/ml of paclitaxel was prepared in acetone. A BETE MicroWhirl® fog nozzle (BETE Fog Nozzle, Inc) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel nanoparticles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours, Paclitaxel nanoparticles produced had an average number-weighted mean size of 0.81 μm with an average standard deviation of 0.74 μm over three separate runs.

Preparation of Docetaxel Particles

A solution of 79.32 mg/ml of docetaxel was prepared in ethanol. The nozzle and a sonic probe were positioned in the pressurizable chamber approximately 9 mm (apart, A stainless steel mesh filter with approximately 100 nm holes was attached to the pressurizable chamber to collect the precipitated docetaxel nanoparticles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 9.5 minutes). The precipitated docetaxel agglomerates and particles were then collected from the supercritical carbon dioxide as the mixture is pumped through the stainless steel mesh filter. The filter containing the nanoparticles of docetaxel was opened and the resulting product was collected from the filter.

Docetaxel nanoparticles produced had an average number-weighted mean size of 0.82 μm with an average standard deviation of 0.66 μm over three separate ethanol runs.

Particle Size Analysis

Particle size was analyzed by both light obscuration and laser diffraction methods. An Particle Sizing Systems AccuSizer 780 SIS system was used for the light obscuration method and Shimadzu SALD-7101 was used for the laser diffraction method. Paclitaxel nanoparticles were analyzed using 0.10% (w/v) sodium dodecyl sulfate (SDS) in water as the dispersant, Docetaxel nanoparticles were analyzed using isopar G as the dispersant.

Paclitaxel suspensions were prepared by adding approximately 7 mL of filtered dispersant to a glass vial containing approximately 4 mg of paclitaxel particles. The vials were vortexed for approximately 10 seconds and then sonicated in a sonic bath approximately 1 minute. If the sample was already suspended, 1:1 solution of paclitaxel suspension to 0.1% SDS solution was made, vortexed for 10 seconds, and sonicated in the sonic bath for 1 minute.

Docetaxel suspensions were prepared by adding approximately 7 mL of filtered dispersant to a plastic vial containing approximately 4 mg of docetaxel particles. The vial was vortexed for approximately 10 seconds and then sonicated in a sonic bath for approximately 2 minutes. This suspension was used for laser diffraction analysis. Unused suspension was poured into a 125 mL particle-free plastic bottle, which was then filled to approximately 100 mL with filtered dispersant. The suspension was vortex for approximately 10 seconds and then sonicated in the sonic bath for approximately 2 minutes. This diluted suspension was used for light obscuration analysis.

A background test was first performed prior to analyzing particles on the AccuSizer 780 SIS. A new particle-free plastic bottle was filled with blank suspension solution by pumping from a reservoir, using a peristaltic pump, through a 0.22 μm Millipore filter and into the bottle. A background analysis was run to ensure the particle/mL count was below 100 particles/mL. A small amount of paclitaxel suspension, 5-100 depending upon concentration of solution, was pipetted into the plastic bottle in place from the background test and was filled with ~100 mL dispersant and the analysis was started. Counts were monitored and paclitaxel solution added to reach and/or maintain 6000-8000 particle counts/mL during the entire analysis. Once the analysis was completed, the background data was removed and any measurement with less than four counts was removed.

To analyze particles on SALD-7101 using a batch cell, the analysis was started by choosing Manual Measurement. The refractive index was set as 1.5 to 1.7. The batch cell was filled with filtered dispersant just past the etched line. The blank measurement was ran. A small amount of API (paclitaxel or docetaxel) suspension was pipetted, generally <1 mL, depending upon concentration of solution as low as 100 μL, into the batch cell as needed to achieve an acceptable absorbance between 0.15 and 0.2 absorbance units. The measurements were executed, and the resulting graph with the highest level of confidence was selected; background was automatically accounted for.

BET Analysis

A known mass between 200 and 300 mg of the analyte was added to a 30 mL sample tube. The loaded tube was then mounted to a Porous Materials Inc. SORPTOMETER®, model BET-202A. The automated test was then carried out using the BETWIN® software package and the surface area of each sample was subsequently calculated.

Bulk Density Analyte

Paclitaxel or docetaxel particle preparations were added to a 10 mL tared graduated cylinder through a plastic weigh funnel at room temperature. The mass of the drug was measured to a nearest 0.1 mg, the volume was determined to the nearest 0.1 mL and the density calculated.

Dissolution Studies

Paclitaxel

Approximately 50 mg of material (i.e.: raw paclitaxel, milled paclitaxel, or paclitaxel particles) were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 μm filter and analyzed on a U(V/V)is spectrophotometer at 227 nm. Absorbance values of the samples were compared to those of standard solutions prepared in dissolution media to determine the amount of material dissolved.

Docetaxel

Approximately 50 mg of material (i.e.: raw docetaxel, milled docetaxel, or docetaxel particles) was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 μm filter, and analyzed on a UV/VIS spectrophotometer at 232 nm. Absorbance values of the samples were compared to those of standard solutions prepared in dissolution media to determine the amount of material dissolved.

Results

The BET surface area of particles produced using the above protocol and variations thereof (i.e.: modifying nozzles, filters, sonic energy sources, flow rates, etc.) ranged between 22 and 39 mm$^2$/g. FIG. 1 shows exemplary particles produced using the methods of the invention. By comparison, the BET surface area of raw paclitaxel was measured at 7.25 m$^2$/g(FIG. 2), while paclitaxel particles made according to the methods of U.S. Pat. Nos. 5,833,891 and 5,874,029 ranged from 11.3 to 15.58 m$^2$/g. Exemplary particle sizes produced using the methods of the invention are shown in Table 1.

TABLE 1

| | Surface area | Mean Size μm | | St Dev μm | |
|---|---|---|---|---|---|
| | m$^2$/g | Number | Volume | Number | Volume |
| 1 | 38.52 | 0.848 | 1.600 | 0.667 | 0.587 |
| 2 | 33.82 | 0.754 | 0.988 | 0.536 | 0.486 |
| 3 | 35.90 | 0.777 | 1.259 | 0.483 | 0.554 |
| 4 | 31.70 | 0.736 | 0.953 | 0.470 | 0.466 |
| 5 | 32.59 | 0.675 | 0.843 | 0.290 | 0.381 |
| 6 | 38.22 | 0.666 | 0.649 | 0.344 | 0.325 |
| 7 | 30.02 | 0.670 | 0.588 | 0.339 | 0.315 |
| 8 | 31.16 | 0.672 | 0.862 | 0.217 | 0.459 |
| 9 | 23.90 | 0.857 | 1.560 | 0.494 | 0.541 |
| 10 | 22.27 | 0.857 | 1.560 | 0.494 | 0.541 |
| 11 | 26.19 | 0.861 | 1.561 | 0.465 | 0.546 |

Comparative studies on bulk density, SSA, and dissolution rates (carried out as noted above) for raw drug, milled drug particles, and drug particles produced by the methods of the present invention are provided in Tables 2 and 3 below. The full dissolution time course for the paclitaxel and docetaxel materials are provided in Tables 4 and 5, respectively.

TABLE 2

| Compound: Paclitaxel | | | | | |
|---|---|---|---|---|---|
| | | Particles | | | |
| Characteristic | Raw Material | Batch 1 | Batch 2 | Mean | Milled |
| Number Mean (um) | 1.16 | 0.83 | 0.67 | 0.75 | 0.89 |
| Volume Mean (um) | 1.29 | 1.42 | 0.57 | 1.00 | 1.35 |
| Bulk Density (g/cm$^3$) | 0.26 | 0.060 | 0.11 | 0.085 | 0.31 |
| Surface Area (m$^2$/g) | 10.4 | 35.6 | 39.8 | 37.7 | 15.0 |
| Dissolution (30 min) | 18% | 42% | 52% | 47% | 32% |

TABLE 3

Compound: Docetaxel

| Characteristic | Raw Material | Particles | | | Milled |
| --- | --- | --- | --- | --- | --- |
| | | Batch 1 | Batch II | Mean | |
| Number Mean (um) | 1.58 | 0.92 | 0.80 | 0.86 | 1.11 |
| Volume Mean (um) | 5.05 | 4.88 | 4.03 | 4.46 | 3.73 |
| Bulk Density (g/cm$^3$) | 0.24 | 0.062 | 0.096 | 0.079 | 0.44 |
| Surface Area (m$^2$/g) | 15.9 | 43.0 | 45.4 | 44.2 | 15.2 |
| Dissolution (30 min) | 11% | 27% | 27% | 27% | 9% |

TABLE 4

Paclitaxel Dissolution time course

| Timepoint (minutes) | Paclitaxel Raw Material | Paclitaxel Particles | Milled Paclitaxel |
| --- | --- | --- | --- |
| 0 | 0.0% | 0.0% | 0.0% |
| 10 | 14.0% | 40.2% | 23.0% |
| 20 | 17.8% | 47.6% | 30.0% |
| 30 | 18.4% | 51.9% | 32.3% |
| 60 | 23.9% | 58.3% | 38.6% |
| 90 | 28.6% | 62.9% | 43.5% |

TABLE 5

Docetaxel Dissolution time course

| Timepoint (minutes) | Docetaxel Raw Material | Docetaxel Particles | Milled Docetaxel |
| --- | --- | --- | --- |
| 0 | 0.0% | 0.0% | 0.0% |
| 5 | 3.2% | 12.1% | 3.2% |
| 15 | 6.9% | 21.7% | 5.9% |
| 30 | 11.2% | 27.2% | 9.3% |
| 60 | 16.4% | 32.9% | 12.2% |
| 120 | 22.4% | 38.9% | 13.6% |
| 225 | 26.8% | 43.1% | 16.0% |

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

We claim:

1. A particle collection device, comprising:
   a vessel defining a chamber, wherein the vessel includes a distal end and a proximal end;
   an inlet port extending from the proximal end of the vessel, wherein the inlet port is in fluid communication with the chamber;
   an outlet port extending from the proximal end of the vessel, wherein the outlet port is in fluid communication with the chamber, and wherein the outlet port includes a porous material positioned between the chamber and the outlet port;
   a collection insert positioned substantially within the chamber; and
   a support frame positioned between an interior wall of the chamber and the collection insert, wherein the support frame comprises:
   a distal ring;
   a proximal ring;
   one or more support legs connecting the distal ring to the proximal ring; and
   a gasket positioned adjacent to the proximal ring.

2. The particle collection device of claim 1, further comprising:
   a sampling tube having a distal end and a proximal end, wherein the proximal end of the sampling tube extends from the proximal end of the vessel, and wherein the distal end of the sampling tube extends into the chamber.

3. The particle collection device of claim 1, wherein the collection insert comprises a plastic bag.

4. The particle collection device of claim 1, wherein the gasket comprises a neoprene gasket.

5. The particle collection device of claim 1, wherein the porous material is selected from the group consisting of a frit, a mesh, and a cloth.

6. The particle collection device of claim 1, wherein the porous material comprises a sintered filter having a distal end and a proximal end, wherein the proximal end of the sintered filter extends from the proximal end of the vessel and is coupled to the outlet port, and wherein the distal end of the sintered filter extends into the chamber.

7. The particle collection device of claim 1, wherein an outer diameter of the inlet port has a range from about 12.7 mm to about 101.6 mm.

8. The particle collection device of claim 1, wherein an outer diameter of the outlet port has a range from about 12.7 mm to about 20.8 mm.

9. The particle collection device of claim 2, wherein an outer diameter of the sampling tube has a range from about 6.35 mm to about 25.4 mm.

10. The particle collection device of claim 1, wherein an outer diameter of the vessel has a range from about 152.4 mm to about 914.4 mm.

11. The particle collection device of claim 1, wherein the inlet port includes a coupling mechanism to connect an outlet of a particle filtration system to the inlet port.

12. The particle collection device of claim 11, wherein the coupling mechanism comprises one or more sanitary fittings.

13. The particle collection device of claim 11, wherein the coupling mechanism comprises one or more compression fittings.

14. A system, comprising the collection device of claim 1 and a non-transitory computer readable medium having stored thereon instructions, that when executed by one or more processors, causes the collection device to:
   receive a plurality of particles through the inlet port of the particle collection device;
   collect the plurality of particles in the chamber of the vessel;
   receive a gas through the inlet port; and
   vent the gas through the porous material and out of the outlet port.

* * * * *